(12) United States Patent
Morcillo Montejo et al.

(10) Patent No.: US 12,360,131 B2
(45) Date of Patent: Jul. 15, 2025

(54) TECHNIQUES FOR CONTROLLING AUTOMATED ANALYZERS USING A SHADOW WORKFLOW ENGINE

(71) Applicant: Roche Diagnostics Operations, Inc., Indianapolis, IN (US)

(72) Inventors: Alejandro Morcillo Montejo, Girona (ES); Marco Maetzler, Belmont, CA (US); Juan Bacardit, Santpedor (ES)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 742 days.

(21) Appl. No.: 17/142,359

(22) Filed: Jan. 6, 2021

(65) Prior Publication Data
US 2021/0215731 A1 Jul. 15, 2021

(30) Foreign Application Priority Data
Jan. 9, 2020 (EP) .................................... 20382009

(51) Int. Cl.
G01N 35/10 (2006.01)
G01N 35/00 (2006.01)
G06F 9/06 (2006.01)
G06F 9/50 (2006.01)

(52) U.S. Cl.
CPC ........... *G01N 35/1002* (2013.01); *G06F 9/06* (2013.01); *G06F 9/5061* (2013.01); *G01N 2035/00514* (2013.01)

(58) Field of Classification Search
None
See application file for complete search history.

(56) References Cited

U.S. PATENT DOCUMENTS

| 2002/0147515 A1 | 10/2002 | Fava et al. |
| 2010/0036956 A1 | 2/2010 | Nishikawa |
| 2014/0129172 A1 | 5/2014 | Eberhardt et al. |
| 2015/0309058 A1 | 10/2015 | Kain et al. |
| 2019/0072575 A1* | 3/2019 | Oosterbroek ...... G01N 35/0092 |
| 2019/0271713 A1 | 9/2019 | Heinemann et al. |

FOREIGN PATENT DOCUMENTS

| EP | 3451253 A1 | 3/2019 |
| WO | 2001/009618 A1 | 2/2001 |

OTHER PUBLICATIONS

European Search Report issued Jun. 22, 2020 in Application No. 20382009.7, 2 pp.
Search Report issued Sep. 5, 2023, in Chinese Application No. 202110022513.2, 2 pp.

* cited by examiner

Primary Examiner — G. Steven Vanni
(74) Attorney, Agent, or Firm — KATTEN MUCHIN ROSENMAN LLP

(57) ABSTRACT

A computer-implemented method for processing biological samples in an environment including multiple automated analyzers having multiple modules is presented. The method includes receiving data related to a plurality of orders for processing biological samples at a main workflow engine. The main workflow engine receives and processes data for each of the multiple automated analyzers having multiple modules. The method further includes providing a data snapshot to at least one shadow workflow engine associated with a subset of one or more modules of the multiple modules. The data snapshot comprises only a portion of the data related to the plurality of orders that is necessary to determine actions of the module of the multiple modules. The method further includes determining, by the shadow workflow engine, a plurality of actions for the subset of modules to process the plurality of orders based on the data snapshot.

17 Claims, 2 Drawing Sheets

TECHNIQUES FOR CONTROLLING AUTOMATED ANALYZERS USING A SHADOW WORKFLOW ENGINE

CROSS-REFERENCE TO RELATED APPLICATIONS

This application claims priority to EP 20382009.7, filed Jan. 9, 2020, which is hereby incorporated by reference.

BACKGROUND

The present disclosure generally relates to methods and systems for controlling the operation of automated analyzers for processing biological samples.

Laboratories hosting automated analyzers for processing biological samples are growing ever bigger and more complex. For instance, automated analyzers and modules thereof are located on different floors, in different buildings or even on different sites of a laboratory. On the other hand, there is an increasing push to provide software solutions for controlling the workflows of such laboratories centrally. This leads to software solutions of increasing complexity causing, inter alia, a considerable volume of network traffic to relay control data to the different automated analyzers. The computing resources required at the centralized control node can also be considerable. The increasing complexity also increases a likelihood of errors when executing the control software and a latency in the system. This might reduce the turnaround times of biological samples (such as patient samples) and reduce the productivity of the automated analyzers. Additionally, having a single central entity driving the whole automation represents a single point of failure for the overall system.

SUMMARY

According to the present disclosure, a computer-implemented method for processing biological samples in an environment including multiple automated analyzers having multiple modules is disclosed. The method can comprise receiving data related to a plurality of orders for processing biological samples at a main workflow engine. Each order can be a request that one or more assays are to be performed on one or more biological samples. The main workflow engine can be configured to receive and process data for each of the multiple automated analyzers having multiple modules. The method can also comprise providing a data snapshot to at least one shadow workflow engine associated with a subset of one or more modules of the multiple modules. The data snapshot can include only a portion of the data related to the plurality of orders that is necessary to determine actions of the module of the multiple modules. The method can also comprise determining, by the shadow workflow engine, a plurality of actions for the subset of modules to process the plurality of orders based on the data snapshot. The shadow workflow engine can be configured to assume the role of the main workflow engine for a limited amount of time. The main workflow engine can be configured to determine the plurality of actions for the subset of modules to process the plurality of orders at the subset of modules in response to a failure at the shadow workflow engine.

Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
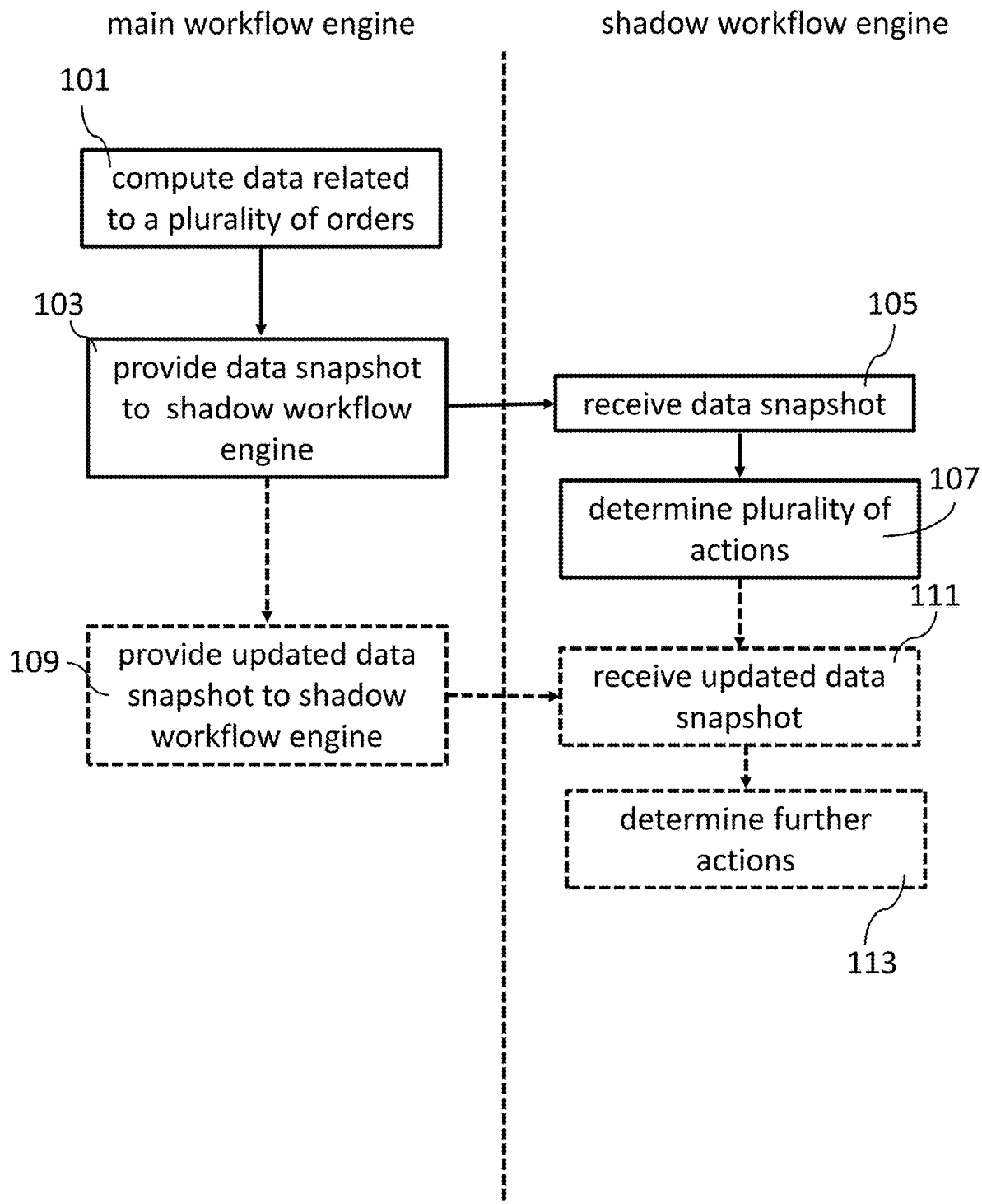
FIG. 1 illustrates a flow diagram of the method for processing biological samples in an environment including multiple automated analyzers having multiple modules according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A computer-implemented method for processing biological samples in an environment including multiple automated analyzers having multiple modules is presented. The method can comprise receiving data related to a plurality of orders for processing biological samples at a main workflow engine. Each order can be a request that one or more assays are to be performed on one or more biological samples. The main workflow engine can be configured to receive and process data for each of the multiple automated analyzers having multiple modules. The method can further comprise providing a data snapshot to at least one shadow workflow engine associated with a subset of one or more modules of the multiple modules. The data snapshot can include only a portion of the data related to the plurality of orders that is necessary to determine actions of the module of the multiple modules. The method can continue with determining, by the shadow workflow engine, a plurality of actions for the subset of modules to process the plurality of orders based on the data snapshot so that then system can reduce the likelihood of failure and increase the scalability and performance of the system. The shadow workflow engine can be configured to assume the role of the main workflow engine for a limited amount of time and/or the main workflow engine can be configured to determine the plurality of actions for the subset of modules to process the plurality of orders at the subset of modules in response to a failure at the shadow workflow engine.

A computer system can be configured to carry out the above method steps.

Particular embodiments of the subject matter of the method and system can be implemented to realize one or more of the following advantages.

Firstly, the techniques of the present disclosure can reduce an amount of communication in a network of the environment including the multiple automated analyzers having multiple modules (e.g., a multi-site or multi-floor laboratory). The shadow workflow engines can operate autonomously (without or with reduced interaction with the main workflow engine) for a predetermined period of time. Moreover, parts of the workflow relevant for a particular subset of modules can be processed locally. This can lead to a reduction of network traffic, particularly in environments including multiple sites and a large number of automated analyzers. In some prior art solutions, the (main) workflow engine can interface with all automated analyzers and their modules to control operation of the automated analyzers.

Secondly, the main workflow engine and the one or more shadow workflow engines can operate simultaneously and (at least partially) independently from each other on different tasks. For instance, a shadow workflow engine can process data (e.g., running simulations or testing new configurations) independently from the main workflow engine. In this manner, the processing workload can be distributed over the environment.

Third, having a main workflow engine and one or more shadow workflow engines can provide redundancy in the environment in some examples. The shadow workflow engine can assume the role of the main workflow engine in some implementations. This can keep the operations running, e.g., for a limited duration until a failure of the main workflow engine can be fixed. On the other hand, the main workflow engine can take over tasks of the shadow workflow engine in case of non-availability of the shadow workflow engine.

A number of terms are used in the present disclosure in a particular way:

The term "automated analyzer" as used herein can refer to any kind of automated or semi-automated technical device to generate measurement results in a laboratory or other health-care related environment. The automated analyzers can be laboratory-automated analyzers or diagnostic automated analyzers in some examples.

A "laboratory automated analyzer" can be any automated analyzer used in laboratory work in the clinical, chemical, biological, immunology or pharmaceutical area or the like. For example, "automated analyzers" can include in-vitro diagnostic analyzers, such as immunochemistry, hematology analyzers or clinical chemistry analyzers.

The term "diagnostic automated analyzer" may not only include automated analyzers used in the process of diagnosing a disease, but also automated analyzers for screening, health classification, risk assessment, monitoring, staging, prediction, prognosis and more. For example, a diagnostic automated analyzer can be an ultrasound device, a radiology device (e.g., an x-ray device, a computer tomography device or a MRI device), an ECG device, an EEG device, or another monitoring device of a bodily function.

"Automated analyzers" may not necessarily be located in a dedicated laboratory or clinical environment. Rather, the term can also include analyzers for carrying out diagnostic or analytic procedures in the clinical, chemical, biological, immunology or pharmaceutical area. For example, a benchtop device in point-of-care settings such as physician clinics or pharmacies or a device for home-use can also be a piece of laboratory equipment according to the present disclosure.

"Automated analyzers" as used herein can comprise a control unit or controller operatively coupled to one or more analytical, pre- and post-analytical modules or work cells wherein the control unit can be operable to control the modules. In addition, the control unit may be operable to evaluate and/or process gathered analysis data, to control the loading, storing and/or unloading of samples to and/or from any one of the analyzers, to initialize an analysis or hardware or software operations of the analysis system used for preparing the samples, sample tubes or reagents for said analysis and the like.

An automated analyzer can include one or more modules. These modules can be configured to carry out any task or activity in a workflow of processing samples in the automated analyzer (or multiple tasks or activities). For example, a module can be a transport module configured to transport samples, consumables (e.g., reagents or other consumables) or other components required to carry out a workflow. For example, a transport module can be configured to transports samples between different analytical modules.

A module can also be a pre-processing or post-processing module configured to carry out pre-processing or post-processing operation required in the workflow. For instance, a pre-processing operation can include one or more of a cleaning, enriching, separating or diluting a sample or an aliquot of a sample.

A module can also be storage module for samples (e.g., a storage module providing a particular storage environment such as a refrigerated environment or another environment with a controlled temperature and/or other controlled parameters).

A module can also be an analytical module. The term "analyzer module"/"analytical module" as used herein can encompass any apparatus or apparatus component that can induce a reaction of a biological sample with a reagent for obtaining a measurement value. An analyzer module can be operable to determine via various chemical, biological, physical, optical or other technical procedures a parameter value of the sample or a component thereof. An analyzer module may be operable to measure the parameter of the sample or of at least one analyte and return the obtained measurement value. The list of possible analysis results returned by the analyzer can comprise, without limitation, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various types. An analyzer module may comprise units assisting with the pipetting, dosing, and mixing of samples and/or reagents. The analyzer may comprise a reagent-holding unit for holding reagents to perform the assays. Reagents may be arranged, for example, in the form of containers or cassettes containing individual reagents or group of reagents, placed in appropriate receptacles or positions within a storage compartment or conveyor. It may comprise a consumable feeding unit. The analyzer module may comprise a process and detection system whose workflow is optimized for certain types of analysis. Examples of such analyzer modules are clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

A "workflow" in the present disclosure can refer to a definition of an orchestrated and repeatable pattern of activity of automated analyzers (and their modules) to process biological samples. A workflow can describe the systematic organization of resources of the automated analyzers into processes that are necessary for processing the biological samples. A workflow can be described as a sequence of operations of one or more automated analyzers. A workflow can be described in any suitable textual or symbolic representation. In one example, a workflow can be described (at least partially) by a decision tree defining which actions an automated analyzer or a module thereof carries out in different situations based on multiple conditions and rules that can be configured by the customer an updated in real-time.

A "workflow engine" can monitor and manage the execution of a workflow in an environment including automated analyzers. The workflow engine can have access to a definition of the configuration and capabilities of the automated analyzers of an environment and a definition of the workflows. The workflow engine can manage and monitor the state of activities or actions in a workflow and determine which new action or activity to transition to according to defined processes. The activities or actions may include transporting biological samples, reagents or other consumables, pre-processing the biological samples, carrying out measurements or tests on the biological samples, processing test results, or any other task of an environment including automated analyzers for processing biological samples described in the present disclosure (or actions or activities forming sub-steps of these tasks).

Workflow engines can carry out two functions in some examples. First, the workflow engine can verify a current process status (e.g., a status of a module of an automated analyzer). After passing the first step, the workflow engine can execute one or more actions or tasks.

A workflow engine can be embodied in any suitable software and hardware environment. In some examples, a workflow engine can be embodied in software running on a general-purpose computer. In other examples, a workflow engine can run on a dedicated piece of hardware.

The term "(computer) network" as used herein can encompass any type of wireless network, such as a WIFI, GSM, UMTS or other wireless digital network or a cable based network, such as Ethernet or the like. In particular, the communication network can implement the Internet protocol (IP). For example, the communication network can comprise a combination of cable-based and wireless networks.

A "control unit" or "controller" can control the automated analyzer in a way that the necessary steps for the processing protocols can be conducted by the automated analyzer. That can mean the control unit may, for example, instruct the automated analyzer to conduct certain pipetting steps to mix the liquid biological sample with reagents, or the control unit can control the automated analyzer to incubate the sample mixtures for a certain time and the like. The control unit may receive information from a data management unit regarding which steps need to be performed with a certain sample. In some embodiments, the control unit might be integral with the data management unit or may be embodied by a common hardware. The control unit may, for instance, be embodied as a programmable logic controller running a computer-readable program provided with instructions to perform operations in accordance with a process operation plan. The control unit may be set up to control, for example, any one or more of the following operations: loading and/or wasting and/or washing of cuvettes and/or pipette tips, moving and/or opening of sample tubes and reagent cassettes, pipetting of samples and/or reagents, mixing of samples and/or reagents, washing pipetting needles or tips, washing mixing paddles, controlling of a light source, e.g., selection of the wavelength, or the like. In particular, the control unit may include a scheduler, for executing a sequence of steps within a predefined cycle time. The control unit may further determine the order of samples to be processed according to the assay type, urgency, and the like.

A "measurement result" of the diagnostic or laboratory-automated analyzer as used herein can be any output of the above listed automated analyzer. Depending on the respective automated analyzer, a measurement result can be obtained by analyzing a life or dead body or a part thereof (e.g., a mammalian patient or a part of a mammalian patient) or a sample (e.g., a biological sample).

For instance, a measurement result can include one or more parameter values measured in a life or dead body or a part thereof or a sample (e.g., a concentration of a particular substance in a blood sample). In other examples, a measurement result can include one or more images of a live or dead body or a part thereof or a sample (e.g., an X-ray or MRI image).

The term "(biological) sample" can refer to material(s) that may potentially contain an analyte of interest. The sample can be derived from a biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The biological sample can be pretreated prior to use, such as preparing plasma from blood. Methods of treatment can involve centrifugation, filtration, distillation, dilution, concentration and/or separation of sample components including analytes of interest, inactivation of interfering components, and the addition of reagents. A sample may be used directly as obtained from the source or used following a pretreatment to modify the character of the sample. In some embodiments, an initially solid or semi-solid biological material can be rendered liquid by dissolving or suspending it with a suitable liquid medium. In some examples, the sample can be suspected to contain a certain antigen or nucleic acid. The term "sample" can be used consistently to refer to different stages of a workflow for the sake of simplicity even if the "physical substrate" of the sample changes, e.g., an aliquot is taken, the sample is diluted or enriched or mixed with a reagent.

The term "order" can include any request for a piece of laboratory equipment to automatically or semi-automatically carry out a particular task. For example, an order can be a request that one or more assays are to be performed on one or more biological samples.

General Overview

Referring initially to FIG. 1, FIG. 1 is a flow diagram of the method for processing biological samples in an environment including multiple automated analyzers having multiple modules.

The method can include computing 101 data related to a plurality of orders for processing biological samples at a main workflow engine. In some examples, the biological samples can be patient samples. In the subsequent sections, the biological samples can from time to time be described as contained in sample tubes (e.g., collection tubes for a biological sample) for the sake of illustration. However, the techniques of the present invention are not limited to control processing of sample tubes in an environment including multiple automated analyzers. Rather, the biological samples can be contained in or carried by any suitable container or substrate. Further examples are discussed below.

Each order can include information specifying how to process a particular sample. In particular, the order can specify which test or assay (or which multiple tests or multiple assays) can be performed on a particular biological sample. In addition, the order can include one or more parameters defining a timing of the processing of the sample (e.g., data indicating a priority of a biological sample or data specifying a particular processing time (a maximum processing time or a particular time of completion) for the biological sample).

The main workflow engine can be configured to receive and process data for each of the multiple automated analyzers having multiple modules. In other words, the main workflow engine can have access to a definition of the configuration and capabilities of all automated analyzers (and their modules) of the environment. The main workflow engine can be configured to determine a sequence of activities or actions of the multiple automated analyzers having multiple modules to process the orders.

The computing can include determining a set of activities or actions for each module to process the orders. For instance, the main workflow engine can determine a sequence of activities or actions to be performed on a patient sample to carry out a particular assay. In some examples, the main workflow engine can be configured to receive orders for processing biological samples at run time to calculate a plurality of actions of the multiple automated analyzers having multiple modules based on a workflow to process the orders.

The main workflow engine can manage and monitor the state of activities or actions in a workflow and determine which new action or activity to transition to according to defined processes for all automated analyzers (and their modules) of the environment. However, in the techniques according to the present disclosure, the main workflow engine can provide 103 a data snapshot to a shadow workflow engine associated with a subset of one or more modules of the multiple modules. The snapshot can then be processed at the shadow workflow engine as discussed below. Additional aspects of the main workflow engine will be also discussed below.

The shadow workflow engine can (as the main workflow engine) manage and monitor the state of activities or actions in a workflow and determine which new action or activity to transition to according to defined processes for automated analyzers (and their modules) of the environment. In some examples, the shadow workflow engine can have the same processing capabilities as the main workflow engine. In other examples, the shadow workflow engine can have limited processing capabilities compared to the main workflow engine. For instance, the shadow workflow engine can be equipped with a more limited amount of computational resources (e.g., processing power or memory). In addition, or alternatively, the shadow workflow engine can be limited in terms of versatility or functionality. For instance, the shadow workflow engine can be configured to only manage and monitor the state of activities or actions in a workflow (or part thereof) and determine which new action or activity relating to the subset of one or more modules of the multiple modules of the environment (e.g., a transport module or multiple transport modules).

The shadow workflow engine can receive 105 the data snapshot. The data snapshot can include only a portion of the information related to the plurality of orders that is necessary to determine actions of the subset of one or more modules of the multiple modules. For instance, the data snapshot can include data concerning actions and activities of the subset of one or more modules the shadow workflow is associated with. In some examples, the snapshot can include one or more of information regarding a workflow state of the workflow, status information regarding one or more modules of the multiple modules, result information, or information related to one or more samples to be processed (e.g., patient information, information regarding the tests or assays to be carried out on one or more samples or priority information for one or more samples).

In some examples, the data snapshot can include information (e.g., data concerning actions or activities) required (e.g., all information required) to process the orders on the subset of one or more modules for a predetermined period of time. In some examples, this period can be at least 5 minutes (e.g., at least 15 minutes or at least 1 hour).

The shadow workflow engine can determine 107 a plurality of actions for the subset of one or more modules to process the plurality of orders based on the data snapshot. For instance, the shadow workflow engine can make decisions regarding in which sequence to execute a plurality of actions on the subset of one or more modules. The shadow workflow engine can manage and monitor the state of activities or actions in a workflow of the subset of one or more modules. For example, the shadow workflow engine can instruct the subset of one or more modules to carry out a predetermined action. The shadow workflow engine can check if the predetermined action has been successfully carried out. If this is the case, the shadow workflow engine can instruct the subset of one or more modules to carry out a next predetermined action. If not, the shadow workflow engine can register an error state and proceed with an error handling routine.

In addition, or alternatively, the shadow workflow engine can process workflow rules or definitions to determine a plurality of actions of the subset of one or more modules based on the data snapshot received. For instance, the data snapshot can include information regarding a workflow state, status information regarding one or more modules of the multiple modules, result information, or information related to one or more samples to be processed which can be processed by applying the workflow rules or definitions to determine a plurality of actions of the subset of one or more modules.

As can be seen, the shadow workflow engine can take over tasks the main workflow engine has to perform in some prior art systems. This can mean that an amount of network traffic can be reduced as some network traffic caused by the main workflow engine (possibly remotely) managing and monitoring the execution of a workflow on the subset of one or more modules can be superseded as the shadow workflow engine takes over some or all responsibilities for managing and monitoring the execution of the workflow. In other examples, network traffic between the main workflow engine and the subset of one or more modules can be controlled more flexibly (but not necessarily be reduced) when using the techniques of the present disclosure. For instance, network traffic can be shifted to periods of time in which a network traffic load on the network of the environment is reduced compared to other periods. In this manner, network congestion can be reduced even if a total amount of network traffic is not reduced in some situations.

In some examples, the shadow workflow engine can be configured to run in a stand-alone manner for a predetermined period of time to process the plurality of orders at the subset of one or more modules. For instance, the predetermined period of time can be at least 10 minutes (optionally at least 30 minutes, further optionally at least 1 hour). This can improve the throughput of the environment including multiple automated analyzers in some examples as a non-availability of one workflow engine—e.g., due to a failure or a maintenance of the respective workflow engine—(be it the main workflow engine or a shadow workflow engine) may still leave the other workflow engines operable (at least for a certain duration).

In some examples, an amount and/or nature of the data included in the data snapshot can be configured at a central management system of the environment including the multiple automated analyzers. For instance, a user may be able to configure a period of time for which the shadow workflow engine can operate in a stand-alone manner. The amount of data in the snapshot can be adjusted accordingly. In some examples, the user can be able to configure a quantity of actions or activities of the subset of modules whose corresponding data is included in the data snapshot.

In some examples, the shadow workflow engine can be configured to operate without communicating with the main workflow engine for a predetermined period of time after having received a data snapshot. The predetermined period of time can be at least 10 minutes, optionally at least 30 minutes, further optionally at least 1 hour.

The data snapshot can be updated 109, 111 at predetermined times. In some examples, changes in the workflow information of the plurality of orders can be propagated to the shadow workflow engine at predetermined times. A frequency and/or scope of updates or propagated changes to the data snapshot can be configurable in some examples. For instance, configuring the update logic can include defining rules governing a timing and/or scope of the updates. In some examples, the rules can take into account computing and networking capabilities of the environment (e.g., to generate an evenly distributed traffic on a network of the environment).

In addition, or alternatively, the update operation of the data snapshot can be event-driven in some examples, the rules can include event-based changes of the updates (e.g., in case of errors in a particular workflow engine or other components of the environment).

In some examples, the shadow workflow engine can be configured to assume the role of the main workflow engine for a limited amount of time. For instance, the shadow workflow engine can be configured to assume the role of the main workflow engine for less than 2 hours, optionally for less than 1 hour, further optionally for less than 30 minutes. In addition or alternatively, the shadow workflow engine can assume the role of the main workflow engine for more than 5 minutes, optionally for more than 30 minutes, further optionally for more than 1 hour.

As discussed above, the shadow workflow engine can have qualitatively or quantitatively the same capabilities as the main workflow engine. In some examples, the shadow workflow engine can be provided with additional data to assume the role of the main workflow engine. This data can be sent to the shadow workflow engine or accessed by the shadow workflow engine in a remote storage location.

The shadow workflow engine can assume the role of the main workflow engine in different situations. In one example, assuming the role of the main workflow engine can happen in response to a loss of connectivity with the main workflow engine. In addition or alternatively, the shadow workflow engine can assume the role of the main workflow engine in response to a non-availability of the main workflow engine, e.g., due to a failure of the main workflow engine. In still other examples, the shadow workflow engine can assume the role of the main workflow engine in case the main workflow engine is updated or modified (and therefore temporarily unavailable).

In this manner, providing a main workflow engine and (one or more) shadow workflow engines can introduce a certain redundancy in the workflow processing of the environment. This can reduce downtime and increase productivity of the environment as a part of the automated analyzers or even all automated analyzers can still remain operable (at least for a certain period of time) in case the main workflow engine fails.

In the same manner (in addition or alternatively), the shadow workflow engine can be configured to redirect the determining of a plurality of actions or activities for the subset of one or more modules to process the plurality of orders at the subset of modules to the main workflow engine in response to a non-availability of the shadow workflow engine (e.g., due to a failure of the shadow workflow engine or due to a maintenance operation of the shadow workflow engine). More generally, the main workflow can take over the tasks of the shadow workflow engine in particular circumstances.

It has been discussed in the preceding passages that the shadow workflow engine and the main workflow engine can be to some extent exchangeable in some situations. However, as also discussed, the shadow workflow engine can have a reduced set of functionalities or capabilities compared to the main workflow engine. In some examples, the shadow workflow engine can be dedicated to manage and monitor only the subset of one or more modules it is associated with (while being incapable of managing and monitoring other subsets of modules).

In addition or alternatively, the main workflow engine can be configured to define and edit rules for determining the workflows of biological samples while the shadow workflow engine is not configured to edit rules for determining the workflow of biological samples.

These and other "reductions in functionality" of the shadow workflow engine can make the shadow workflow engine a small footprint unit in some examples which can be implemented and run at different locations of the environment without creating an undue overhead in resources.

Further Aspects of Environments Including Main and Shadow Workflow Engines

Further aspects of environments including a main workflow engine and a shadow workflow engine will be discussed subsequently in connection with FIG. 2.

In the preceding sections, different aspects of the main workflow engine and the shadow workflow engine have been discussed based on the example of a single shadow workflow engine. However, the technique of the present disclosure can include setting up multiple (e.g., more than 10 or more than 20) shadow workflow engines associated with different subsets of one or more modules in some examples.

In this case, the techniques of the present disclosure can include providing a second data snapshot to a second shadow workflow engine associated with a second subset of one or more modules of the multiple modules. The second subset of modules can be different from the subset of modules a first shadow workflow engine is associated with. The second data snapshot can include only a portion of the data that is necessary to determine actions of the second subset of modules of the multiple modules. The second shadow workflow engine can determine a plurality of actions for the second subset of modules to process the plurality of orders based on the second data snapshot.

Accordingly, the techniques of the present disclosure can include providing further data snapshots to further shadow workflow engines associated with further subset of modules of the multiple modules (e.g., one, two three, or more than three further subsets of modules). Again, the further data snapshots can each include only a portion of the data that is necessary to determine actions of the further subset of modules of the multiple modules. Each further shadow workflow engine can determine a plurality of actions for the respective further subset of modules to process the plurality of orders based on the respective further data snapshots.

Each shadow workflow engine can be configured to receive the data snapshots and to calculate a plurality of actions of respective one or more modules to process the orders. The shadow workflow engines can be configured to run (at least partially) simultaneously to determine actions for the respective modules.

Figure 2:
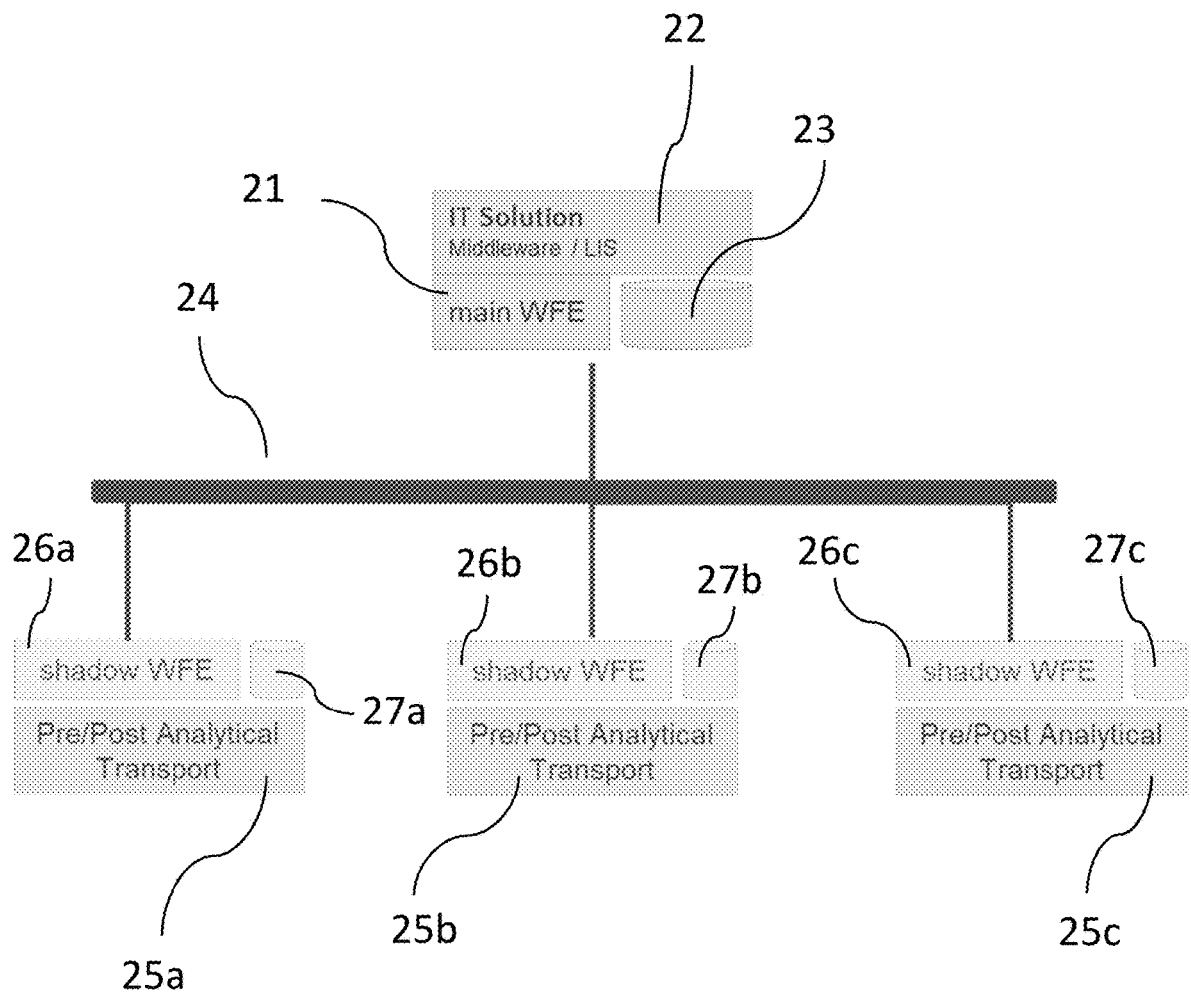
FIG. 2 illustrates a diagram illustrating a main workflow engine and multiple shadow workflow engines according to an embodiment of the present disclosure.

FIG. 2 depicts an example environment including a main workflow engine 21 and multiple shadow workflow engines 26a, 26b, 26c. The workflow engines can be connected via a network 24 of the environment.

The main workflow engine 21 can be connected to a data storage 23 including a complete set of data for processing orders in the environment according to one or more predetermined workflows. For example, the data storage 23 can include all workflow definitions and rules of the one or more workflows (e.g., in the form of decision trees defining the workflows). In addition, the data storage 23 can include state variables describing a configuration of the environment. In addition or alternatively, the data storage 23 can include one or more of information related to one or more samples to be processed, patient information related to one or more samples to be processed, results of tests or assays for samples or other information to be used for carrying out the one or more workflows in the environment.

In the example of FIG. 2, the main workflow engine can be integrated in a middleware layer 22 of the environment (e.g., a laboratory information system "LIS"). However, the main workflow engine can be hosted elsewhere in other examples.

Each shadow workflow engine 26a-c can be associated with a respective subset of one or more modules 25a, 25b, 25c. As depicted in FIG. 2, the modules can be pre-analytical or post analytical modules, transport modules for transporting the biological samples, storage modules (e.g., fridge modules) or analytical modules (e.g., any of the modules discussed above). In one example, the environment or part of it can be configured to process biological samples contained in sample tubes. In this example, a transport module can be configured to convey the sample tubes between other modules (e.g., from a pre-analytical module to an analytical module or between two different analytical modules).

As explained, each of the shadow workflow engines 25a-c can be connected to a data storage 27a, 27b, 27c including a respective of data required to process orders at the respective subset of modules 25a-c associated with the respective shadow workflow engine 25a-c provided as data snapshots as discussed in the present disclosure. The data snapshots in the data storages 27a-c can be provided and updated as discussed above.

The different subsets of one or more modules can be set up in different ways depending on the environment.

In some examples, a first subset of the automated analyzers or modules can be located at a first location of the environment and a second subset of the automated analyzers can be located at a second location remote from the first location. The first and second locations can be first and second rooms, first and second floors, first and second buildings or first and second sites.

In addition or alternatively, a first subset of the automated analyzers or modules can belong to a first processing line of the environment and a second subset of the automated analyzers or modules can belong to a second processing line different from the first processing line. In some examples, each processing line can include a particular set of modules to carry out a task. For example, an environment can include multiple sets of modules each forming a production line for testing biological sample by one or more particular assays. In addition or alternatively, different production lines can be equipped with different types of modules. For instance, each of the different production lines can include modules configured to carry out a different assay or test (or different sets of assays or tests). In still other examples, different production lines can include analytical modules of different types (e.g., an immunochemistry analytical module, a clinical chemistry analytical module, an analytical module including a mass spectrometer or other types of analytical modules).

In other examples, different subsets of modules, each associated with a shadow workflow engine, can perform sub-steps in a sample processing process of a production line. For instance, a subset of modules associated with a shadow workflow engine can be associated with a central sampling unit for transferring biological sample from a first vessel into a second vessel (e.g., a reaction vessel). In other examples, a subset of modules associated with a shadow workflow engine can be associated with a central sample distribution module distributing samples to different analytical modules. In still other examples, a subset of modules associated with a shadow workflow engine can be transport modules configured to transport samples between different analytical or other modules of a production line.

In general, the orders for processing biological samples can require transportation of samples through and processing of the samples in a plurality of modules of the multiple modules. Transporting the biological samples or other components (e.g., reagents or consumables) within a potential widespread environment including multiple automated analyzers can be a challenging task. On the other hand, it may be required that an environment (e.g., a laboratory) meets certain targets in terms of e.g., turnaround time.

The workflow engines of the present disclosure can be configured so that processing orders meet one or more predetermined targets.

In some examples, the workflow engines can be configured to locate a sample and secure that the biological samples arrive at particular modules of the multiple modules at a scheduled time.

In other examples, the workflow engines can be configured to locate a sample and secure that the biological samples arrive at particular modules of the multiple modules no later than at a particular time.

In still other examples, the workflow engines can be configured to realize a particular maximum sample processing time for particular biological samples. For instance, the workflow engines can be configured to secure that an order to process a particular sample (or type of samples) is completed no later than a predetermined period of time after the order was received.

Similar targets can be set for consumables and/or reagents required to process orders in the environment including multiple automated analyzers.

As discussed above, the biological samples of the present disclosure can be contained in sample tubes in some examples. The sample tubes can be transported between different pre-analytical modules, analytical modules or post-analytical modules. In other examples, the biological samples can be contained in other containers or vessels (e.g., vials, bottles or bags). In still other examples, the biological sample can be supported on a suitable support structure (e.g., a slip, a dish or a plate). In the course of processing the orders, biological sample can be transferred between containers or supports of the same or different types.

Computer Implementation

In the preceding sections, the main and shadow workflow engines have been described mostly by discussing their functionality. As already stated, the main and shadow workflow engines can be implemented in any suitable hardware and/or software environment.

The present disclosure can relate to a computer system being configured to carry out the steps of any one of the methods for processing biological samples in an environment including multiple automated analyzers having multiple modules.

For instance, the main workflow engine can be implemented in a central computer system controlling the environment (e.g., a laboratory). For instance, the main workflow engine can be implemented in a middleware layer of the environment (e.g., a Hospital Information System, Laboratory Information System or as a separate element of the laboratory middleware called Laboratory Automation System which will interact with the Laboratory Management System).

The shadow workflow engines described herein can reside in a dedicated piece of hardware associated with the respective subset of one or more modules. In some examples, the shadow workflow engine can be implemented on a stand-alone processor associated with the respective subset of one or more modules.

In other examples, the shadow workflow engine can be installed on a general-purpose computing system connected to the respective subset of one or more modules.

Further disclosed and proposed is a computer program including computer-executable instructions for performing the method according to the present disclosure in one or more of the embodiments disclosed herein when the program is executed on a computer or computer network. Specifically, the computer program may be stored on a computer-readable data carrier. Thus, specifically, one, more than one or even all of method steps as disclosed herein may be performed by using a computer or a computer network, preferably by using a computer program.

Further disclosed and proposed is a computer program product having program code, in order to perform the method according to the present disclosure in one or more of the embodiments enclosed herein when the program is executed on a computer or computer network. Specifically, the program code may be stored on a computer-readable data carrier.

Further disclosed and proposed is a data carrier having a data structure stored thereon, which, after loading into a computer or computer network, such as into a working memory or main memory of the computer or computer network, may execute the method according to one or more of the embodiments disclosed herein.

Further disclosed and proposed is a computer program product with program code stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Further disclosed and proposed is a modulated data signal, which contains instructions readable by a computer system or computer network, for performing the method according to one or more of the embodiments disclosed herein.

Referring to the computer-implemented aspects of the present disclosure, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing measurements.

Further disclosed and proposed is a computer or computer network comprising at least one processor, wherein the processor can be configured to perform the method according to one of the embodiments described in this description.

Further disclosed and proposed is a computer loadable data structure that can be configured to perform the method according to one of the embodiments described in this description while the data structure is being executed on a computer.

Further disclosed and proposed is a storage medium, wherein a data structure can be stored on the storage medium and wherein the data structure can be configured to perform the method according to one of the embodiments described in this description after having been loaded into a main and/or working storage of a computer or of a computer network.

An allocation topology (environment including networks) is not included for simplicity. The main and shadow workflow engines may communicate (but not limited to) via physical networks (unique or multiplexed) or using secure virtual private networks or through the cloud using encrypted channels tunneling the data and encrypting the payload information with custom certificates.

Further Aspects

In the preceding detailed description multiple examples of methods and systems for processing biological samples in an environment including multiple automated analyzers having multiple modules have been discussed. However, the methods and systems for processing biological samples in an environment including multiple automated analyzers having multiple modules of the present disclosure can also be configured as set out in the following.

A computer-implemented method for processing biological samples in an environment including multiple automated analyzers having multiple modules is presented. The method can comprise receiving data related to a plurality of orders for processing biological samples at a main workflow engine, wherein the main workflow engine can be configured to receive and process data for each of the multiple automated analyzers having multiple modules, providing a data snapshot to at least one shadow workflow engine associated with a subset of one or more modules of the multiple modules, wherein the data snapshot can include only a portion of the data related to the plurality of orders that is necessary to determine actions of the module of the multiple modules, and determining, by the shadow workflow engine, a plurality of actions for the subset of modules to process the plurality of orders based on the data snapshot.

The method can further comprise updating the data snapshot at predetermined times.

Changes in the data related to the plurality of orders can be propagated to the shadow workflow engine at predetermined times. A frequency and/or scope of updates or propagated changes to the data snapshot can be configurable.

The shadow workflow engine can be configured to run in a stand-alone manner for a predetermined period of time to process the plurality of orders at the subset of modules. The predetermined period of time can be at least 10 minutes, optionally at least 30 minutes, or further optionally at least 1 hour.

An amount of data included in the data snapshot can be configured at a central management system of the environment including the multiple automated analyzers.

The shadow workflow engine can be configured to assume the role of the main workflow engine for a limited amount of time.

The method can further comprise the shadow workflow engine assuming the role of the main workflow engine for at least 2 hours, optionally for at least 1 hour, further optionally for at least 30 minutes, or optionally for between 30 minutes and 3 hours.

The shadow workflow engine can assume the role of the main workflow engine in response to a loss of connectivity with the main workflow engine.

The shadow workflow engine can assume the role of the main workflow engine in response to a non-availability of the main workflow engine.

The shadow workflow engine can be configured to redirect the determining of a plurality of actions for the subset of modules to process the plurality of orders at the subset of modules to the main workflow engine in response to a failure at the shadow workflow engine.

The method can further comprise providing a second data snapshot to a second shadow workflow engine associated with a second subset of one or more modules of the multiple modules, the second subset of modules being different from the above subset of modules, wherein the second data snapshot includes only a portion of the data that is necessary to determine actions of the second subset of modules of the multiple modules, and determining, by the second shadow workflow engine, a plurality of actions for the second subset of modules to process the plurality of orders based on the second data snapshot.

The method can further comprise providing further data snapshots to further shadow workflow engines associated with further subset of one or more modules of the multiple modules, the further subset of modules being different from the above subset of modules, wherein the further data snapshots each include only a portion of the data that is necessary to determine actions of the further subset of modules of the multiple modules, and determining, by the further shadow workflow engines, a plurality of actions for the respective further subset of modules to process the plurality of orders based on the respective further data snapshots.

The shadow workflow engines can be configured to run simultaneously to determine actions for the respective subset of modules.

The main workflow engine can be configured to define and edit rules for determining the workflow of biological samples.

The shadow workflow engine may not be configured to define and edit rules for determining the workflow of biological samples.

The main workflow engine can access a definition of capabilities and a current configuration of each automated analyzer of the automated analyzers having multiple modules of the environment.

The shadow workflow engine can be configured to operate without communicating with the main workflow engine for a predetermined period of time after having received a data snapshot. The predetermined period of time is at least 10 minutes, optionally at least 30 minutes, or further optionally at least 1 hour.

A first subset of the automated analyzers or modules can be located at a first location of the environment and a second subset of the automated analyzers or modules can be located at a second location remote from the first location, or a first subset of the automated analyzers or modules can belong to a first processing line of the environment and a second subset of the automated analyzers or modules can belong to a second processing line different from the first processing line. The first and second locations can be first and second rooms, first and second floors, first and second buildings or first and second sites.

The shadow workflow engine can reside in a dedicated piece of hardware associated with the respective subset of one or more modules.

The shadow workflow engine can be installed on a general-purpose computing system connected to the respective subset of one or more modules.

The main workflow engine can be configured to receive data related to orders for processing biological samples at run time to calculate a plurality of actions of the multiple automated analyzers having multiple modules based on a workflow to process the orders. The main workflow engine can be configured to determine a sequence of actions of the multiple automated analyzers having multiple modules to process the orders. Each shadow workflow engine can be configured to receive the data snapshots and to calculate a plurality of actions of respective one or more modules to process the orders. Each shadow workflow engine can be configured to instruct the respective subset of modules to perform the plurality of actions.

The orders for processing biological samples can require transportation of samples through and processing of the samples in a plurality of modules of the multiple modules.

The plurality of modules can include one or more of a pre-processing module, a sample preparation module, a transport module, an analytical module for performing an analytical function and a post-processing module.

The workflow engines can be configured to locate the sample and secure that the biological samples arrive at particular modules of the multiple modules at a scheduled time.

The workflow engines can be configured to realize a particular maximum sample processing time for particular biological samples.

A computer system being configured to carry out the steps of the above methods.

A computer-readable medium having instructions stored thereon which when executed by a computer system prompt the computer system to execute the steps of the above methods.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A computer-implemented method for processing biological samples in an environment including multiple automated analyzers having multiple modules, the method comprising:
receiving data related to a plurality of orders for processing biological samples at a main workflow engine, wherein each order is a request that one or more assays are to be performed on one or more biological samples and wherein the main workflow engine is configured to receive and process data for each of the multiple automated analyzers having multiple modules;
providing a data snapshot to at least one shadow workflow engine associated with a subset of one or more modules of the multiple modules, wherein the data snapshot includes only a portion of the data related to the plurality of orders that is necessary to determine actions of the module of the multiple modules; and
determining, by the shadow workflow engine, a plurality of actions for the subset of modules to process the plurality of orders based on the data snapshot, wherein the shadow workflow engine is configured to assume the role of the main workflow engine for a limited amount of time, and/or wherein the main workflow engine is configured to determine the plurality of actions for the subset of modules to process the plurality of orders at the subset of modules in response to a failure at the shadow workflow engine, and
wherein the shadow workflow engine is not configured to edit rules for each of the multiple automated analyzers having multiple modules.

2. The method according to claim 1, further comprising, updating the data snapshot at predetermined times.

3. The method according to claims 1, wherein the shadow workflow engine is configured to run in a stand-alone manner for a predetermined period of time to process the plurality of orders at the subset of modules.

4. The method of claim 3, wherein the predetermined period of time is at least 10 minutes.

5. The method of claim 3, wherein the predetermined period of time is at least 30 minutes.

6. The method of claim 3, wherein the predetermined period of time is at least 1 hour.

7. The method according to claim 1, wherein the shadow workflow engine assumes the role of the main workflow engine in response to a loss of connectivity with the main workflow engine, or wherein the shadow workflow engine assuming the role of the main workflow engine in response to a non-availability of the main workflow engine.

8. The method according to claim 1, wherein the main workflow engine has access to a definition of the configuration and capabilities of all automated analyzers and their modules of the environment and wherein the main workflow engine is configured to determine a sequence of activities or actions of the multiple automated analyzers having multiple modules to process the orders.

9. The method according to claim 1, wherein the shadow workflow engine is configured to manage and monitor the state of activities or actions in a workflow of the subset of one or more modules.

10. The method according to claim 1, further comprising:
providing a second data snapshot to a second shadow workflow engine associated with a second subset of one or more modules of the multiple modules, the second subset of modules being different from the subset of modules of claim 1, wherein the second data snapshot includes only a portion of the data that is necessary to determine actions of the second subset of modules of the multiple modules; and
determining, by the second shadow workflow engine, a plurality of actions for the second subset of modules to process the plurality of orders based on the second data snapshot.

11. The method according to claim 10, wherein the shadow workflow engines are configured to run simultaneously to determine actions for the respective subset of modules.

12. The method according to claim 1, wherein the main workflow engine is configured to define and edit rules for determining the workflow of biological samples processing data inputs in real-time.

13. The method according to claim 1, wherein the shadow workflow engine is configured to operate without communicating with the main workflow engine for a predetermined period of time after having received a data snapshot.

14. The method according to claim 1, wherein a first subset of the automated analyzers or modules is located at a first location of the environment and a second subset of the automated analyzers or modules is located at a second location remote from the first location, or a first subset of the automated analyzers or modules belongs to a first processing line of the environment and a second subset of the automated analyzers or modules belongs to a second processing line different from the first processing line.

15. The method according to claim 1, wherein the multiple modules include one or more of a pre-processing module or a transport module for an analytical module for performing an analytical function.

16. A computer system comprising a main workflow engine and at least one shadow workflow engine configured to carry out steps of:
receiving data related to a plurality of orders for processing biological samples at the main workflow engine, wherein each order is a request that one or more assays are to be performed on one or more biological samples and wherein the main workflow engine is configured to receive and process data for each of the multiple automated analyzers having multiple modules;
providing a data snapshot to the at least one shadow workflow engine associated with a subset of one or more modules of the multiple modules, wherein the data snapshot includes only a portion of the data related to the plurality of orders that is necessary to determine actions of the module of the multiple modules; and
determining, by the at least one shadow workflow engine, a plurality of actions for the subset of modules to process the plurality of orders based on the data snapshot, wherein the shadow workflow engine is configured to assume the role of the main workflow engine for a limited amount of time, and/or wherein the main workflow engine is configured to determine the plurality of actions for the subset of modules to process the plurality of orders at the subset of modules in response to a failure at the shadow workflow engine, and
wherein the shadow workflow engine is not configured to edit rules for each of the multiple automated analyzers having multiple modules.

17. A non-transitory computer-readable medium having instructions stored thereon which when executed by a computer system prompt the computer system to execute steps of:
receiving data related to a plurality of orders for processing biological samples at the main workflow engine, wherein each order is a request that one or more assays are to be performed on one or more biological samples and wherein the main workflow engine is configured to receive and process data for each of the multiple automated analyzers having multiple modules;

providing a data snapshot to the at least one shadow workflow engine associated with a subset of one or more modules of the multiple modules, wherein the data snapshot includes only a portion of the data related to the plurality of orders that is necessary to determine actions of the module of the multiple modules; and determining, by the at least one shadow workflow engine, a plurality of actions for the subset of modules to process the plurality of orders based on the data snapshot, wherein the shadow workflow engine is configured to assume the role of the main workflow engine for a limited amount of time, and/or wherein the main workflow engine is configured to determine the plurality of actions for the subset of modules to process the plurality of orders at the subset of modules in response to a failure at the shadow workflow engine, and wherein the shadow workflow engine is not configured to edit rules for each of the multiple automated analyzers having multiple modules.

\* \* \* \* \*